United States Patent [19]
Lee

[11] 3,947,964
[45] Apr. 6, 1976

[54] JAW MOVEMENT RECORD MEMBER

[76] Inventor: Robert L. Lee, 22937 Grand Terrace Road, Colton, Calif. 92324

[22] Filed: July 1, 1974

[21] Appl. No.: 484,617

[52] U.S. Cl. .................................................. 32/19
[51] Int. Cl.² ......................................... A61C 9/00
[58] Field of Search ..................... 32/32; 46/24, 19

[56] References Cited
UNITED STATES PATENTS
3,577,673    5/1971    Monestier .............................. 46/24

Primary Examiner—Robert Peshock
Attorney, Agent, or Firm—Knobbe, Martens, Olson, Hubbard & Bear

[57] ABSTRACT

A transparent plastic block into which jaw movement information is to be drilled is formed with a small diameter hole perpendicular to the recording surfaces of the member to serve as an index to the accuracy of the recording operation. Score lines on the recording surfaces intersecting the hole center line serve as a further accuracy guide. Score lines on the surfaces of the member facilitate observation of the information recorded in the member.

10 Claims, 8 Drawing Figures

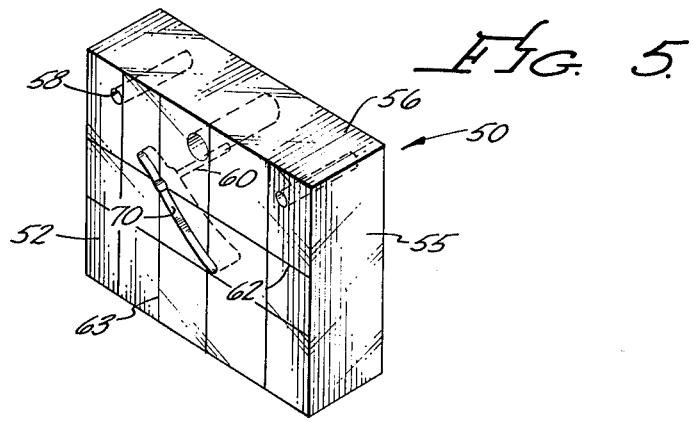
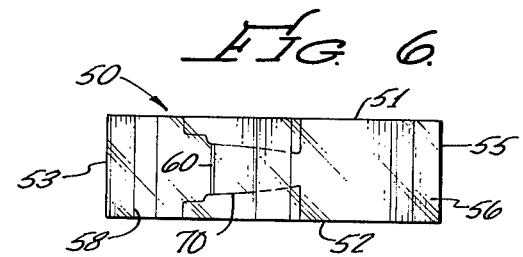
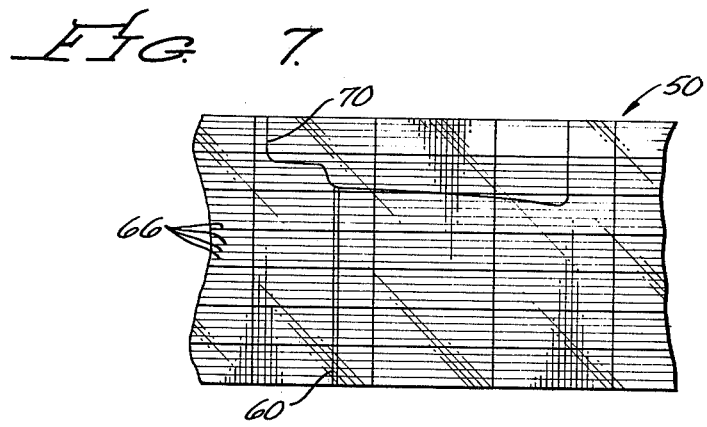
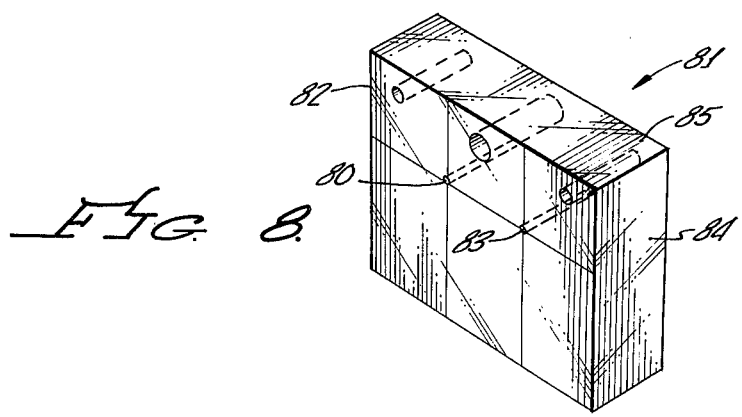

JAW MOVEMENT RECORD MEMBER

In U.S. Pat. No. 3,452,439 issued to Robert L. Lee, the same inventor as the present invention, there is disclosed a system for measuring, recording, and reproducing the jaw movements of a human being. In accordance with that system, jaw movement information is recorded in a primary set of plastic blocks or record members by means of drills which are mounted to move with the lower jaw while the record members are fixed with respect to the upper jaw. The recorded information is ultimately utilized to produce three-dimensional pathways in a second set of plastic blocks which serve to guide the movements of the mandibular frame of an articulator. The present invention relates to improvements in the primary plastic record members in which the information is first recorded on the patient.

In the system described in the aforementioned Lee patent, some of the information which is desired to be recorded is the protrusive movement of the lower jaw. It is necessary that the movement be started from centric position, i.e. where the lower jaw is in its rearwardmost or most retruded position and is centered with respect to the upper jaw. If the recording in the primary blocks is not accurate, the resulting secondary blocks which are to simulate the patient's jaw motions in an articulator will likewise by inaccurate. The system previously utilized is quite reliable if done carefully but there are possibilities for error; and if an error does occur there is no way for the operator to detect the error.

The present invention solves this problem by providing simple but important improvements to the record member. The primary improvement is the provision of a small diameter hole in the record member. This hole is formed prior to the commencement of the recording operation and extends completely through the record member. The hole centerline is aligned colinear with the centric axis position when the record member is fixed with respect to the upper jaw. Such an index hole tells the operator whether the drilling operation is started in the right location and further tells whether the drilling operation is correctly performed, in that the relation between the drilled cavity can be compared with relation to the index hole. This is easily done since the record member is made of transparent material.

As a further improvement, score lines are formed in the surface of the record member intersecting the center line of the index hole so that again the operator can determine whether the drill is properly aligned even after a portion of the index hole has been eliminated by the drilling operation. As another step, score lines are formed on one or more edges of the record member parallel to the surface of the record member in which the drilling occurs. These score lines are preferably equally spaced by some suitable increment such as 1 millimeter. This arrangement enables the operator to quickly visually determine the depth of the drilled cavity at any location in the cavity. Further, it readily enables the operator to compare differences between record members of different patients or differences between record members taken from the same patient before and after treatment for dental defects.

For a more thorough understanding of the invention, reference may be had to the following drawings in which:

FIG. 5 is a perspective view of the member after a completed drilling operation in one side;

FIG. 6 is an edge elevational view showing two of the cavities formed in the record member;

FIG. 7 is an enlarged, elevational view of a portion of the record member of FIG. 5 showing a cavity drilled therein; and FIG. 8 is a perspective view of a record member with two index holes.

Figure 1:
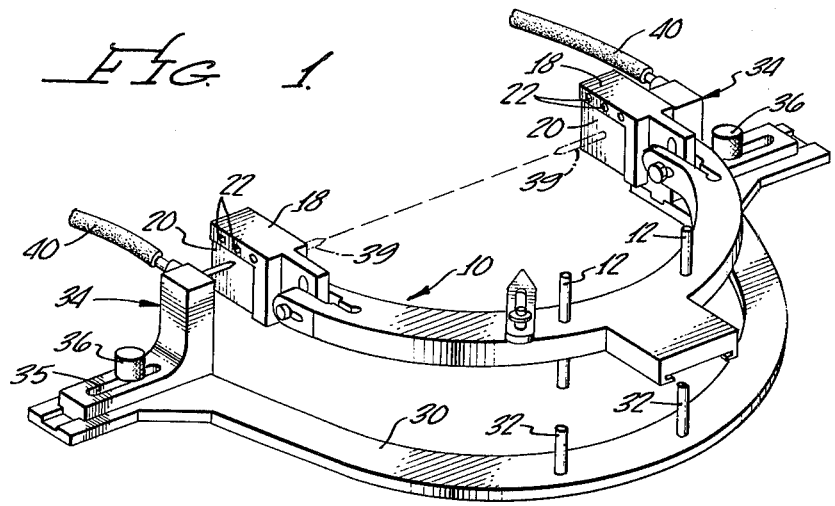
FIG. 1 is a perspective view of apparatus with which the improved record member may be utilized.

Referring first to FIG. 1, there is shown a portion of the apparatus utilized in recording jaw movements as disclosed in the above mentioned Lee patent. This includes a rigid U-shaped upper face bow 10 having a pair of pins 12 vertically extending through forward portions of the face bow to be attached to an upper clutch (not shown) which is utilized to mount the upper face bow to the patient's upper teeth. Also mounted near the forward portion of the upper face bow is a pointer 14 to engage a spot on the patient's nose utilized in establishing a horizontal plane of reference for the jaw movements.

Mounted to the rearward side of the face bow are a pair of recording boxes 18. Alignment blocks 20 of generally rectangular configuration are mounted in the recording boxes 18 by means of a plurality of threaded fasteners 22 extending through an upper flange in the recording box and through suitable apertures in the alignment blocks.

Positioned below the upper face bow 10 is a rigid lower face bow 30 also having a generally U-shaped configuration. Vertically oriented pins 32 in the forward portion of the lower face bow 30 are utilized to attach a suitable clutch (not shown) which in turn is attached to the patient's lower teeth. On the rearward ends of the lower face bow 30 are mounted drill carriages 34 which are laterally adjustable by means of a slot 35 and a threaded fastener 36 extending through the slot and into the face bow. A drill 38 mounted in each of the drill carriages extends towards the upper face bow and into a mating aperture in the alignment blocks. Suitable means 40 extend into the drill carriages for providing power to drive the drills.

Figure 2:
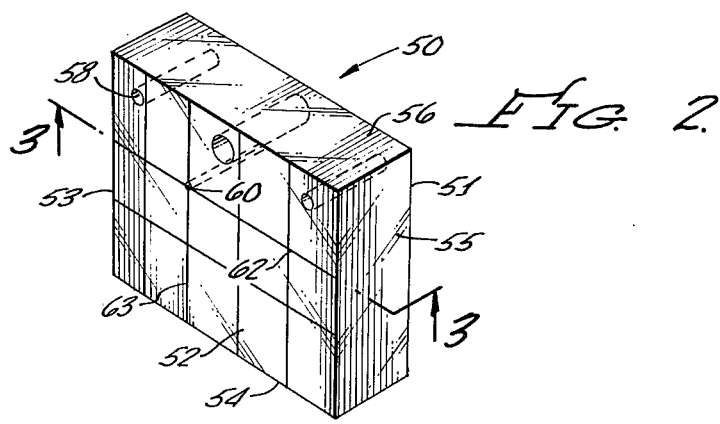
FIG. 2 is a perspective view of the record member with the index hole formed therein.
Figure 3:
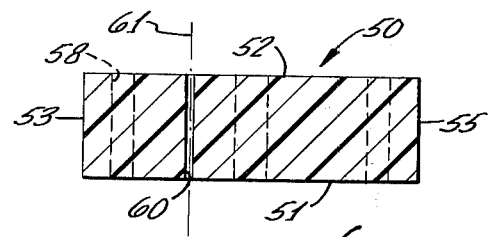
FIG. 3 is a cross-sectional view on line 3—3 of the record member of FIG. 2.

Referring now to FIG. 2, the record block 50 of the invention is seen to have a generally rectangular configuration with a flat inner or medial surface 51 parallel to a flat outer or lateral surface 52. These surfaces are joined by flat, parallel side edges 53 and 55 and flat, parallel lower and upper edges 54 and 56. Three mounting holes 58 extend through the record member 50 from the lateral to the medial surfaces 52 and 51 perpendicular to these surfaces. The holes 58 are spaced and sized to fit with the holes through the recording boxes. The height of the recording member is substantially greater than its lateral thickness, and its length dimension between the side edges 53 and 55, or as measured in a direction from front to rear of the face of the subject, is substantially greater than its height. The record member 50 is made of a rigid transparent plastic material such as polyester fiberglass resin.

In accordance with the invention, there is formed a small diameter index hole 60 extending from the lateral to the medial surface parallel to the surfaces. This index hole is preferably located somewhat above the center of the laterally outward face of the record block and also somewhat to the rear thereof or to the left as viewed in FIG. 2, to provide space for recording the protrusive movement in the record member. The center line of the index hole 60 is the same distance from the mounting holes 58 as the alignment hole in the alignment block 20 is from its mounting holes, so that the alignment hole and the index hole would be completely aligned if mounted in the guide box 18.

As a further reference feature, score lines 62 and 63 are formed in the lateral and medial surfaces of the record member intersecting the center line 61 of the index hole 60. Additionally a plurality of spaced parallel score lines 66 are formed on the top, bottom and side edges of the record member 50. These score lines are preferably equally spaced a convenient increment of length such as 1 millimeter.

Turning now to the use of the record members, as a first step it is necessary to locate the terminal hinge axis position of the patient. This is done by known techniques and reference marks are made on the sides of the patient's face at the points where the hinge axis would intersect the skin. A similar mark is made in the region of the nose in order to establish an orbital axis reference plane. The upper face bow 10 is then positioned on the patient and aligned with the reference marks. To facilitate this, a pair of alignment pins 39 shown in phantom in FIG. 1 are positioned in the holes in the alignment blocks 20 and the inner ends of the pins are aligned with the skin spots on the patient's hinge axis. Further the nose pointer 14 is aligned with the skin spot on the nose. Note that the two axis alignment pins 39 are made to be colinear with each other before joining the bow to the subject's head, as indicated by the broken line 39a in FIG. 1. With the bow so aligned, it is carefully positively attached to the upper teeth by means of a clutch (not shown) using known plaster techniques. As mentioned above the clutch is connected to the vertical mounting pins 12 extending through the face bow. The connection between the clutch and the vertical pins is also adjustable to further help the alignment procedure.

The alignment pins 39 are then removed from the alignment blocks and the lower face bow 30 is positioned on the patient with the drills extending from the drill carriages into the holes in the alignment blocks. The vertical pins 32 in the forward portion of the lower face bow 30 are attached to a suitable clutch (not shown) which is positioned in the patient's mouth to be attached to the patient's lower teeth. However before fixing the lower clutch to the lower teeth, the lower jaw is first moved to centric position. The lower face bow 30 of course moves with the jaw since the drills are positioned in the alignment blocks. With the lower jaw and the lower face bow so positioned, the lower face bow is fixed to the lower jaw by suitable hardening compounds between the clutch and the teeth. The drills can then be withdrawn from the upper bow and the lower jaw is free to move with the lower bow attached to it. The alignment blocks 20 are then removed from the upper face bow and replaced with the plastic record members by means of the two mounting dowel holes and a threaded fastener 22. The foregoing steps are all disclosed in greater detail in the above mentioned Lee patent.

The recording of the jaw movement information can now commence. The drilling operation is typically started by returning the lower jaw to centric position and moving the drill inwardly into the plastic record member 50. It is critical that the drilling actually start in the centric position so that the recorded information is accurate. However if there are no markings on the record member there is no way to know for certain whether the lower jaw is in centric position when the drilling is commenced. The aforementioned Lee patent suggests using a dimple in the record member as an indicator which is helpful, but the dimple is removed by the drilling and does not tell whether the drill is perpendicular to the record member. With the index hole preformed in the record member and accurately aligned with the skin spots by virtue of its relationship to the alignment blocks, the operator can easily and quickly tell whether the lower face bow has been properly fixed to the patient's lower jaw with the drills on the hinge axis when the lower jaw is in centric position. With the index hole the operator can initially tell whether the tip of the drill is aligned with the index hole as the drill approaches the surface of the recording block; and after the drilling operation is started the operator can see whether the drills are properly perpendicularly aligned to the record members, as may be seen from FIG. 4. Without the index hole being there, the operator would not know for certain whether the drills were entering the record blocks in the proper perpendicular manner even though they may have been close to the right spot when the drilling step was commenced.

Figure 4:
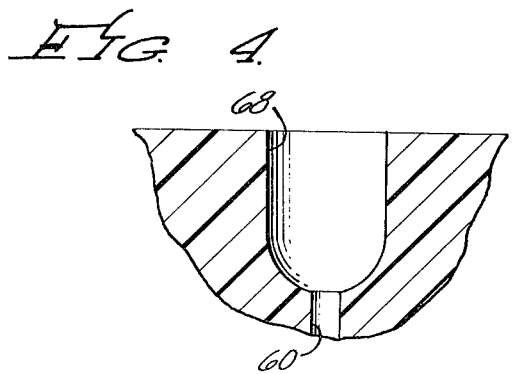
FIG. 4 is an enlarged, fragmentary, cross-sectional view of the record member after the drilling operation in the member has commenced.

Note from FIG. 4, that the diameter of the cavity 68 and thus the drill is considerably larger than the diameter of the index hole 60. This ensures that the drill is not trapped by the index hole 60 and will move with the patient's jaw. Preferably, the index hole is no more than half the diameter of the drill bit.

It is desirable to have the index hole even though care was taken to properly align the drills when the lower face bow was attached to the lower jaw because there are possible errors that may enter the operation. For example, when the lower jaw was supposed to be in centric relation position before the face bow was firmly fixed to the lower jaw, it may not have really been there. With some patients it is not always easy to move the lower jaw to the centric position. Thus when the drilling operation is to commence and the lower jaw is moved to the proper centric relation position, the operator can easily see that something is wrong if the drill is not aligned with the index hole.

Another possible source of error is that the lower jaw might drift while the plaster compound attaching the lower clutch to the teeth is hardening even though the jaw may have initially been in the proper centric relation position. Similarly, other of the many adjustable connections in the system might slip or loosen at any time even though they were initially correctly aligned and even though no slippage occurred during the hardening of the clutch plaster. Thus with the index hole in the recording the operator can know with positive assurance whether the drills and the record members are properly aligned in centric position. This will insure accuracy of the recording operation and therefore prevent error in the resulting simulated joints which are prepared from the information stored in the record member.

Once the drilling step is started and assuming the drill was fairly close to being properly aligned, the index hole is drilled away such that it is not quite so easy to tell from the exterior of the block whether the drilling was started in proper alignment. The score lines 62 and 63 formed in the lateral surface of the block help to verify this in that they should be like a hairline target intersecting the initial hole drilled.

The edge score lines 66 are convenient for making observations of the passages drilled into the record members both during the operation and after completion. Referring to FIG. 6, the operator can quickly determine the actual depth of the cavity 70 drilled into the record member at any location simply by observing the cavity through the surfaces of the record member and counting the number of score lines. Also such lines are quite convenient for comparing two record members. For example, in some operations a record member will be prepared for a particular patient, treatment will be determined and given and then another record member will be prepared to see the effectiveness of the treatment. This can quickly be checked by holding the transparent record members in surface to surface relation with the engravings properly aligned and then by simply noting the differences or by counting the score lines. It is also helpful in some situations to be able to quickly have a numerical value for the depth of the cavity at a certain location for properly setting a dental articulator. For example, the depth of the initial hole drilled in centric position is a starting measure of the immediate side shift of the patient's lower jaw. This dimension is commonly utilized in setting a dental articulator.

Note also from FIGS. 5 and 7 that after a recording of a particular movement has been made on one side of the record member the record member may be positioned on the other side of the patient's face so that the recording of a different movement may be made in a single record member. In addition to thus having the information conveniently available, the recordings for the two sides can be easily compared because of the transparent material utilized. If desired, additional score lines may be formed on the lateral and medial surfaces of the record member to further facilitate noting the differences between the recordings of the patient's jaw joints.

Likewise, additional score lines may be formed on the edges perpendicular to the lines 66. As shown in FIG. 8, it is also possible to have two index holes in the same block, one at either end. Thus the blocks could be reversed on one side of the head in order to accept two different jaw motions. In other words, the index hole 80 in the record member 81 is the same distance from the side edge 82 as the second index hole 83 is from the other side edge 84; and both holes 80 and 83 are equally spaced from the upper edge 85 of the member 81. Also the index holes 80 are similarly positioned with respect to the symmetrically arranged mounting holes 86. Consequently, if the record member 81 is reversed from the position shown in FIG. 8, the index hole 83 would occupy precisely the same location as that occupied by the index hole 80 as shown.

What is claimed is:

1. In dental apparatus for obtaining jaw movement information including a frame to be attached to a person's maxilla, a dental record member mounted on said frame to overlie the person's temporomandibular joint, and means mounted to move with the person's mandible including drill means for recording in said record member jaw movement information, the improvement wherein said record member is a block of transparent rigid material such as polyester fiberglass resin, said record member having a pair of flat parallel surfaces which are mounted perpendicular to the person's jaw hinge axis through said joint, said record member further having means formed therein for mounting the member on said frame and having a small diameter hole extending through the block perpendicular to said surfaces as an accuracy index so that during the entire drilling operation it can be seen whether the drill bit is properly aligned, thereby assuring the accuracy of the recording.

2. The apparatus of claim 1 wherein said index hole is considerably smaller in diameter than the diameter of a drill bit utilized for drilling into the member during the recording operation such that the index hole does not interfere with the tip of the drill bit during the drilling.

3. The apparatus of claim 2 wherein said index hole diameter is no more than about half the diameter of the drill bit to be utilized.

4. The apparatus of claim 1 including a pair of score lines on each of said surfaces intersecting the center line of the index hole.

5. The apparatus of claim 1 including a plurality of side edges joining said surfaces, and a plurality of spaced score lines formed in at least one of said edges to facilitate observations of the recordings to be made in the record member.

6. The apparatus of claim 5 wherein said score lines are equally spaced some convenient unit of measurement such as millimeters.

7. The apparatus of claim 1 including a second index hole parallel to the first mentioned hole, said holes being spaced sufficiently so that the record member can be reversed and information regarding a second jaw movement can be drilled into said member.

8. The apparatus of claim 7 wherein said record member has a rectangular shape with first and second spaced parallel side edges joined by an upper edge and a lower edge, all of said edges being perpendicular to said surfaces, the first mentioned index hole being positioned predetermined distances from said first side edge and said upper edge, and said second hole being positioned said predetermined distances from said second side edge and said upper edge respectively.

9. The apparatus of claim 7 wherein said mounting means is formed so that the member can be reversed on its mounting and wherein said index holes are positioned with respect to said mounting means such that the second index hole will occupy the former position of the first mentioned index hole when the member is reversed on its mounting.

10. The apparatus of claim 9 wherein said member has a rectangular shape with first and second space parallel side edges joined by an upper edge and lower edge, all of said edges being perpendicular to said surfaces, the first mentioned index hole being positioned predetermined distances from said first side edge and said upper edge, and said second hole being positioned said predetermined distances from said second side edge and said upper edge respectively, said index hole being considerably smaller in diameter than the diameter of a drill bit utilized for drilling into the member during the recording operation such that the index hole does not interfere with the tip of the drill bit during the drilling, said member includes a pair of score lines on each of said surfaces intersecting the center line of each of said index holes, said member having a plurality of spaced scorelines formed in at least one of said edges to facilitate observations of the recordings to be made in the record member.

* * * * *